United States Patent
Scelles et al.

(10) Patent No.: US 12,396,896 B2
(45) Date of Patent: Aug. 26, 2025

(54) COMPRESSION GARMENT THAT IS EASY TO SLIP ON/OFF

(71) Applicant: THUASNE, Levallois Perret (FR)

(72) Inventors: Hervé Scelles, Saint Just Saint Rambert (FR); Bruno Mourier, Aboen (FR); Guillaume Labbe, La Talaudiere (FR); Pascal Motet, Saint Etienne (FR)

( * ) Notice: Subject to any disclaimer, the term of this patent is extended or adjusted under 35 U.S.C. 154(b) by 751 days.

(21) Appl. No.: 17/257,347

(22) PCT Filed: May 27, 2019

(86) PCT No.: PCT/FR2019/051223
§ 371 (c)(1),
(2) Date: Dec. 31, 2020

(87) PCT Pub. No.: WO2020/008121
PCT Pub. Date: Jan. 9, 2020

(65) Prior Publication Data
US 2021/0267810 A1    Sep. 2, 2021

(30) Foreign Application Priority Data
Jul. 5, 2018    (FR) ...................... 1856206

(51) Int. Cl.
*A61F 13/08*    (2006.01)
*A41B 11/00*    (2006.01)

(52) U.S. Cl.
CPC .............. *A61F 13/08* (2013.01); *A41B 11/00* (2013.01); *A41B 2400/32* (2013.01); *A41B 2500/10* (2013.01)

(58) Field of Classification Search
CPC ..... A61F 13/08; A41B 11/00; A41B 2400/32; A41B 2500/10
See application file for complete search history.

(56) References Cited

U.S. PATENT DOCUMENTS

| 2,985,001 A | | 5/1961 | Lamontagne et al. |
| 4,067,209 A | * | 1/1978 | Kucera ................. D04B 21/14 297/DIG. 5 |
| 4,228,640 A | * | 10/1980 | Talbot .................... D02G 3/346 57/208 |
| 6,430,970 B1 | | 8/2002 | Gardon-Mollard et al. |

(Continued)

FOREIGN PATENT DOCUMENTS

| CN | 1220593 A | 5/1996 |
| CN | 1308514 A | 8/2001 |

(Continued)

OTHER PUBLICATIONS

English language abstract of CN1220593A.

*Primary Examiner* — Khoa D Huynh
*Assistant Examiner* — Erick I Lopez
(74) *Attorney, Agent, or Firm* — Cabinet Beau de Loménie

(57) ABSTRACT

A compression garment that is easy to slip on/off comprising a compression knitted piece comprising at least one stitch ground yarn and at least one elastic yarn, in particular inlaid yarn, and at least one hairy yarn knitted into the knitted piece so that the knitted piece has, according to all or part of its inner face and of its outer face, hairs projecting from the latter, said hairs being configured so as to be oriented in the direction in which the knitted piece is slipped on and/or off.

21 Claims, 3 Drawing Sheets

(56) References Cited

U.S. PATENT DOCUMENTS

| | | |
|---|---|---|
| 6,811,870 B2 | 11/2004 | Zafiroglu |
| 6,916,301 B1 | 7/2005 | Clare |
| 6,927,182 B2 | 8/2005 | Rock et al. |
| 8,172,782 B2 | 5/2012 | Rock |
| 8,317,736 B2 | 11/2012 | Virkus |
| 8,484,940 B2 * | 7/2013 | Bruner .................. D04B 1/04 139/393 |
| 9,180,027 B2 | 11/2015 | Kettwig et al. |
| 10,954,614 B2 | 3/2021 | Giorgini |
| 2004/0107553 A1 * | 6/2004 | Goineau ................. D02G 3/34 28/247 |
| 2006/0085894 A1 | 4/2006 | Yakopson |
| 2011/0015668 A1 | 1/2011 | Cros |
| 2016/0076175 A1 * | 3/2016 | Rock ........................ D04B 1/18 66/196 |
| 2016/0184777 A1 * | 6/2016 | Cote .................... B01D 69/085 156/390 |
| 2016/0304310 A1 * | 10/2016 | Xia ........................ D02G 1/04 |

FOREIGN PATENT DOCUMENTS

| | | |
|---|---|---|
| CN | 101980676 A | 3/2008 |
| CN | 101842049 A | 9/2010 |
| CN | 107624041 A | 1/2018 |
| DE | 102012024781 | 6/2014 |
| DE | 102012024781 A1 | 6/2014 |
| EP | 0818567 | 1/1998 |
| EP | 0818567 A1 | 1/1998 |
| EP | 1895036 A1 | 3/2008 |
| FR | 2432867 | 3/1980 |
| FR | 2432867 A1 | 3/1980 |
| FR | 2879901 | 6/2006 |
| FR | 2879901 A1 | 6/2006 |
| JP | 2006219805 | 8/2006 |
| JP | 2006219805 A | 8/2006 |
| JP | 2014094112 | 5/2014 |
| JP | 2014094112 A | 5/2014 |

* cited by examiner

COMPRESSION GARMENT THAT IS EASY TO SLIP ON/OFF

BACKGROUND

The present disclosure relates to the technical field of compression garments that are easy to slip on/off.

Compression garments—socks or knee-highs, stockings, tights or sleeves—are used to prevent or treat venous circulation problems, in particular in the lower or upper limbs, as well as pathologies related to lymphatic system dysfunction, and to reduce edemas. Venous disorders can have several origins, including in particular: a stiffening of the vein wall, an alteration of the valves or an increase in the diameter of the veins.

The local pressure exerted on a limb by a compression garment is a function in particular of the force-extension characteristics of said garment.

The pressure exerted on a limb is calculated by Laplace's law as follows: $P \text{ [Pa or mmHg]} = (T \text{ [N]} \times n / (L \text{ [m]} \times R \text{ [m]}))$.

P represents the pressure exerted at a given point on the limb in question.

L is the width of the considered area of the limb and n represents the number of layers of the compression garment disposed on said area.

T is the tension, expressed in newtons, exerted by said garment when it is slipped onto the lower or upper limb.

R is the radius of curvature at the relevant point of the lower or upper limb.

The greater the deficiency in the venous system, the more difficult it is for blood to flow back from the ankle to the heart, and the greater the pressure to be exerted at the ankle.

By way of example in the French system, the compression levels can be distributed as follows:

| Class I:   | 13 to 20 hPa     | Class II: | 20.1 to 27 hPa |
|------------|------------------|-----------|-----------------|
| Class III: | 27.1 hPa to 48 hPa | Class IV: | above 48 hPa   |

Compression garments, in particular of a high class, are difficult for the patient to slip on, in particular when the patient has reduced mobility.

Usually, medical compression stockings include two yarns, namely a weft yarn and a stitch yarn. The weft yarn is an elastic yarn whose path is almost linear in the direction of the rows of stitches of the compression garments. The weft yarn gives the compressive effect to the compression garment. The stitch yarn, also called the ground yarn, gives the knitted compression garment its dimensions as well as its comfort and aesthetic properties.

One criterion for the effectiveness of compression garments is perfect patient compliance with the treatment. Many patients are looking for compression garments that are pleasant to the touch, i.e., soft, and easy to slip on. Being easy to slip on and off is a particularly important parameter for patients with trophic disorders, i.e. for example related to a venous ulcer, lymphedema, and/or with motor problems.

The search for comfort and ease of slipping on should not however be to the detriment of the therapeutic effectiveness, in particular of the compression applied, or of the durability of the compression garment.

Known for example are toe glides placed on the ends of the foot, making it easier to slip on the open-toed compression garment. The disadvantage of these toe glides is that they are only suitable for open-toe compression garments so that the toe glides can be removed once the compression garment has been slipped on.

Also known are support devices allowing the compression garment to be placed in tension on the support device and then the patient's leg to be inserted into the compression garment supported by this device.

The previous devices are tedious to implement and cannot be slipped off. Furthermore, there are medical devices, of the shoehorn type, specifically designed to assist in the removal of compression garments.

Also known are double-compression garments, i.e., comprising a first layer that is easy to slip on without any compressive effect, and a second compression layer that slides against the first layer positioned on the limb to be treated. These garments have the disadvantage that they are thicker, thus less aesthetic, and warmer. In addition, the second layer may tend to slide over the first layer when worn, so the compression garment no longer exerts the therapeutic effect for which it was placed.

EP 2.348.902 B1 relates to a compression garment for sports use with pile only on the inside to improve thermal insulation. The pile formation techniques used allow the formation of the pile only on one face of the textile, (shaving of the loops or cutting of the binding yarns joining two superimposed textiles for a velvet textile). The pile is thus formed on the inner face of the textile.

However, in the case of medical compression garments, it is sought instead that they are lightweight, breathable and do not provide an additional thermal insulation function since they are generally worn underneath clothing.

SUMMARY

The present disclosure aims to provide a compression garment, in particular a medical compression garment, that is easy to slip on/off, the means making it easy to slip on and off being arranged directly in the compression garment without the need for an external device that is complex to implement.

The present disclosure aims to provide a compression garment whose comfort when worn is improved, in particular the feel, in particular of the inner face of the compression garment coming into contact with the skin.

The present disclosure has as its object, according to a first aspect, a compression garment that is easy to slip on/off comprising a compression knitted piece comprising at least one stitch ground yarn and at least one elastic yarn, in particular weft yarn.

Advantageously, the knitted piece comprises at least one hairy yarn, knitted into the knitted piece, so that the knitted piece has, according to all or part of its inner and outer faces, hairs projecting from the latter, said hairs being configured so as to be oriented in the direction in which the knitted piece is slipped on/off.

The inventors discovered that the hairs naturally adopts an arrangement corresponding to the direction of slipping on or off, and flattens on the inner face of the knitted piece, creating an inner face whose surface is smooth. The smooth surface of the inner face of the knitted piece thus has a low coefficient of friction.

Knitting a hairy yarn involves the arrangement of a multiplicity of hairs on both the inner and outer faces.

A knitted hairy yarn is understood to mean any yarn with hairs projecting along its length and configured to be used on a knitting machine. In particular, hairy knitted yarn can be a yarn forming stitches (loop stitches and/or tuck stitches) and/or a weft yarn.

The hairy yarn may be distinct from the stitch ground yarn and/or weft yarn.

The hairy knitted yarn may be inelastic.

In the present text, inelastic yarn means any yarn having an elongation at break of less than or equal to 100%, preferably less than or equal to 50%, and more preferably less than or equal to 30%.

The knitted piece includes rows of stitches, in particular arranged in the transverse direction T of the knitted piece, and wales of stitches, in particular arranged in the longitudinal direction L of the knitted piece.

Stitch ground yarn or stitch yarn is understood to mean any knitted yarn that forms loop stitches and/or tuck stitches.

Weft yarn is understood to mean a yarn inserted into the rows of stitches of the knitted piece, in particular without forming loop stitches, preferably with floats and/or tucks.

In the present text, compression knit garment or piece means any garment or piece of knitted fabric having a compressive or restraining effect.

A compression garment comprising a compression knitted piece is defined as any garment whose knitted piece comprises at least one tubular portion intended to be disposed around at least a portion of a limb on which compression is to be exerted.

The knitted piece can be obtained by assembling, for example by sewing, different knitted panels, or be a unitary knitted piece.

The tubular portion can be obtained seamlessly in one piece (in particular by knitting a tube portion) or is formed by joining the corresponding edges of the unitary knitted piece, for example by sewing or knitting on the knitting machine.

When the knitted piece includes a toe, the latter can be closed when knitting or sewing.

The knitted piece therefore may be selected from: a stocking, a knee-high, a sock, tights, a sleeve for the forearm or arm, or a combination thereof.

Advantageously, hairs formation does not depend on a particular knitting technique. The knitted piece according to the disclosure can thus be knitted on a flat or circular knitting machine.

The knitted piece has opposite inner and outer faces, the inner face being intended in operation to come against the skin.

Advantageously, the hairy yarn is manufactured by knitting before the step of knitting the knitted piece.

In an embodiment, the stitch ground yarn has a titer greater than or equal to 50 dtex and less than or equal to 650 dtex.

In an embodiment, the knitted piece comprises an elastic stitch ground yarn and optionally an inelastic stitch ground yarn.

Elastic yarn in the context of the present disclosure, in particular with regard to the elastic stitch ground yarn and/or the weft yarn (in particular the core of the weft yarn), comprises any yarn having an elongation at break greater than or equal to 300%, preferably greater than or equal to 400%, and more preferably greater than or equal to 500%.

The elongation at break can be determined, for example, using the standard ISO 2062:2009.

In a variant, the hairy yarn comprises a core and hairs projecting from said core.

The yarn thus advantageously has a good mechanical resistance. In addition, it is possible to adjust the length (mm) and the hairs density (number of hairs per linear meter of core or hairy yarn) on the core.

The hairy yarn according to the disclosure is thus an assembly of a core and a hairs cover projecting from the latter providing a velvet effect to the inner and outer faces of the knitted piece.

The core of the hairy yarn, and/or, the hairs of the hairy yarn, and/or, the ground stitch yarn, and/or, the cover yarn(s) of the elastic core of the weft yarn when elastic, comprise(s) one or more multifilament yarn(s) and/or spun yarn(s) of fibers whose constituent material(s) is/are selected from a list I including synthetic materials and a list II including natural or artificial materials.

List I thus includes the following materials: polyesters, in particular polyethylene terephthalate; polyamides, in particular polyamide 6-6; polyolefins, in particular polypropylene and polyethylene, or a mixture thereof; preferably polyethylene terephthalate.

List II includes the following materials: cotton, linen, regenerated cellulose, or a mixture thereof; in particular viscose and/or wool.

Advantageously, the construction of the hairy yarn allows the hairs and the core to be in different yarn structures and materials, which allows differentiating the functions of the hairs from the core structure.

The hairs may be distributed in sections or segments of yarn projecting according to the core of the hairy yarn, again these sections may comprise/be made up, in particular each, of a first end joined to the core of the hairy yarn, and a second free end configured to adopt a direction corresponding to the direction of slipping on or off.

Thus, a yarn section may comprise a plurality of hairs, the number and individual titer of which are a function of the number and individual titer of each of the fibers and/or filaments that the yarn used for the section comprises.

In a variant, the core of the hairy yarn is knitted.

This arrangement improves its strength, in particular its mechanical resistance.

The yarn or yarns from which the hairs are formed may be anchored during the knitting of the hairy yarn, in particular at the same time as the knitting of the core.

In a variant, the core is a pillar stitch in which the hairs are anchored.

The pillar stitch is by definition made of warp stitches and therefore run-resistant, which further improves the mechanical strength of the hairy yarn and the pulling resistance of the hairs in the knitted core.

In a variant, the core of the hairy yarn is knitted with or more multifilament yarn(s) or spun yarn(s) of fibers, or a mixture thereof.

In a variant, the number of hairs sections per centimeter measured along the length of the hairy yarn is greater than or equal to 3, preferably less than or equal to 20, more preferably less than or equal to 15, more preferentially less than or equal to 10.

The hairs density should be sufficient to facilitate slipping on/off, but still limited, because the thermal insulation function is not desired.

In a variant, the knitted piece comprises:
a. at least one row of stitches T comprising at least one inlaid elastic yarn,
b. at least two rows of stitches M1 and M2, each comprising at least one hairy yarn forming stitches, said at least one row of stitches T being disposed between adjacent rows M1 and M2, and the length of at least 80% by number of the hairs of said at least one hairy yarn in at least one of the rows of stitches M1 and M2 is greater than or equal to the distance (d) separating the rows of stitches M1 and M2.

Advantageously, the hairs cover the inlaid elastic yarn, which reduce or even eliminate the shearing effect of the inlaid elastic yarn since the hairs will come between the skin and the area of the knitted piece containing the inlaid elastic yarn.

The shearing effect is mainly provided by the weft elastic yarns, which shear effect is a brake on slipping on and off.

In a variant, the length of at least 80% in number of hairs per centimeter measured along the length of the hairy yarn is greater than or equal to 1 mm, preferably greater than or equal to 5 mm, more preferably greater than or equal to 10 mm, in particular less than or equal to 30 mm, for example of the order of 2 mm f 7%.

In an embodiment, the length of at least 80% in number of hairs per centimeter measured along the length of the hairy yarn is less than or equal to 10 mm.

This measurement can be made by observation with a microscope, and is based on the average of at least ten measurements taken in three different regions along the length of the hairy yarn, each of which is one centimeter long.

In a variant, the hairy yarn is manufactured by knitting on a crochet knitting machine.

This technique makes it possible to form a run-resistant core in which the hairs are anchored when knitting the hairy yarn and thus to vary the length and density of the hairs as desired.

In a variant, the hairy yarn forms stitches, in particular loop stitches and/or tuck stitches.

In a variant, the knitted piece includes a inlaid hairy yarn.

In a variant, the elastic yarn comprises an elastic core and one or more cover yarn(s), and the hairy yarn is a yarn selected from said cover yarn(s).

In a variant, the elastic yarn includes an elastic core and one or more cover yarn(s), and the core has a titer less than or equal to 740 dtex.

The elastic core may have a titer greater than or equal to 200 dtex, more preferably greater than or equal to 350 dtex, preferentially greater than or equal to 500 dtex.

In a variant, the hairy yarn has a titer greater than or equal to 15,000 Nm, in particular greater than or equal to 20,000 Nm, in particular less than or equal to 30,000 Nm.

The hairy yarn must have a fineness adapted to the gauge of the knitted piece.

In a variant, the hairy yarn has a titer greater than or equal to 30,000 Nm, and optionally less than or equal to 100,000 Nm.

In this case, the knitted piece has a higher gauge than when the hairy yarn has a fineness of less than 30,000 Nm.

The present disclosure has as its object the use of a hairy yarn, to facilitate slipping on and/or off, in the knitting of a compression knitted piece for the manufacture of a compression garment, said knitted piece comprising at least one stitch ground yarn and at least one elastic yarn, in particular weft yarn, said at least one hairy yarn is knitted into the knitted piece so that the knitted piece has, according to all or part of its inner face and its outer face, hairs projecting therefrom, said hairs being arranged so as to be oriented in the direction in which the knitted piece is slipped on or off.

The compression garment reproduces, and thus said at least one hairy yarn and the knitted piece reproduce, indifferently, any one of the embodiments, variants or definitions described with reference to a first aspect of the disclosure.

In a variant, the knitted piece is made on a circular knitting machine or on a flat knitting machine, and the hairy yarn is made in a knitting step, in particular on a crochet knitting machine, prior to the step of knitting the knitted piece.

DESCRIPTION OF THE FIGURES

The present disclosure will be better understood upon reading the description of examples of embodiments according to the disclosure cited in a non-limiting manner and illustrated by the following figures and in which.

DETAILED DESCRIPTION

Figure 1:
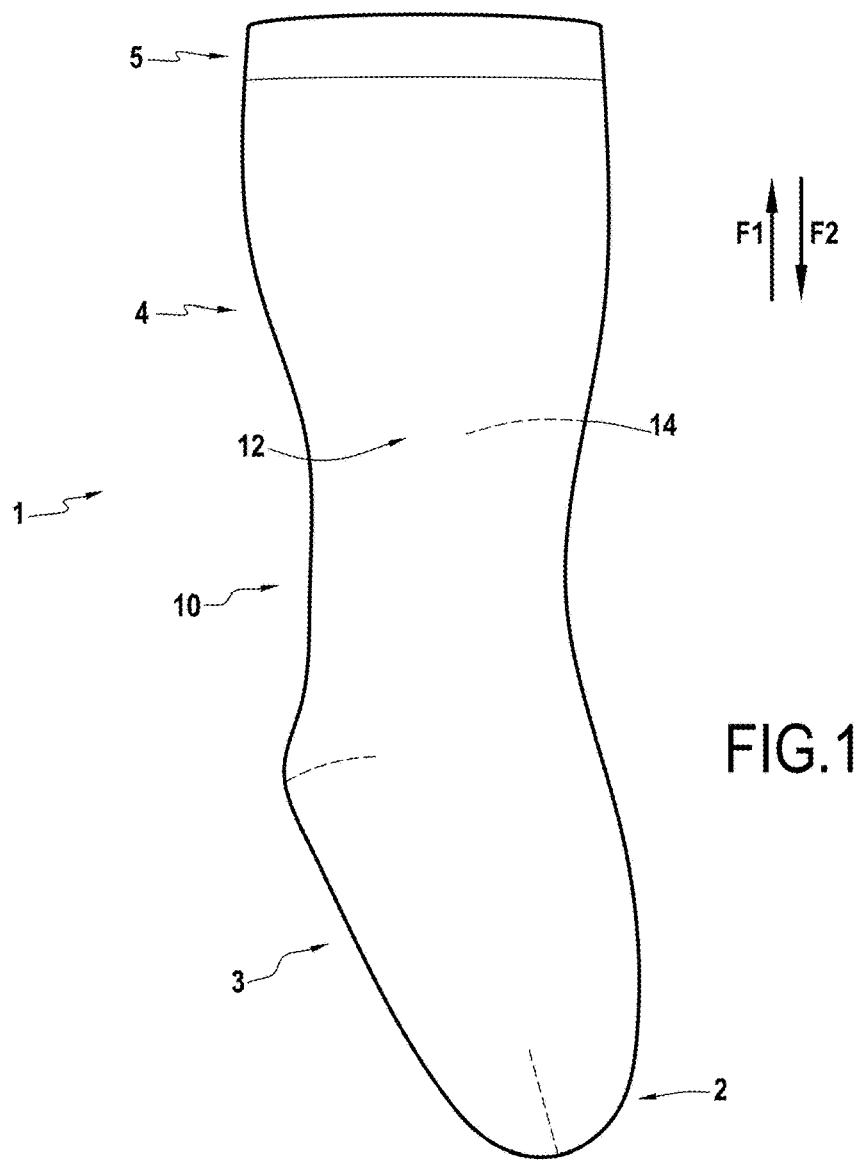
FIG. 1 is a schematic front view of a first example of a compression garment according to the disclosure.
Figure 2:
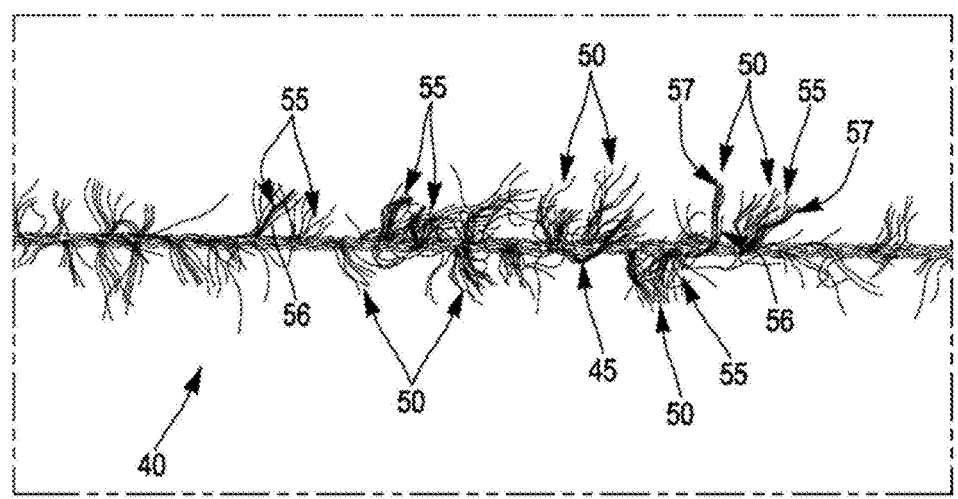
FIG. 2 is a representation of a photograph of an example of hairy yarn according to the disclosure.

The easy on/off compression 1 garment shown in FIG. 1 is a compression sock 1 comprising a compression knitted piece 10, made entirely by knitting.

This knitted piece 10 includes a toe part 2, which may be closed after knitting (for example by sewing), a knitted foot part 3, and in its extension a part corresponding to the knitted leg 4 ending with a cuff 5.

This knitted piece 10 comprises a stitch ground yarn 20, in particular elastic, an inlaid elastic yarn 30, and a hairy yarn 40 knitted into knitted piece 10 in such a way that knitted piece 10 has, according to all or part of its inner face 12 and its outer face 14, hairs 50 projecting from the latter, said hairs 50 being configured in such a way as to orient itself in the direction of slipping on F1 and/or of F2 of the knitted piece 10. The hairs 50 are distributed in sections 55 or segments 55 of yarns projecting from the core 45 of the hairy yarn 40. These sections 55 may comprise/be each made up of a first end 56 joined to the core 45 of the hairy yarn, and a second free end 57 configured to adopt a direction corresponding to the direction of slipping on or off. The hairy yarn 40 comprises a core 45 and hairs 50 projecting from said core 45. The core 45 is knitted. Additionally, the core 45 may be knitted including a pillar stitches in which the hairs 50 are anchored. The core 45 of the hairy yarn 40 is knitted with multifilament yarns and/or spun yarns of fibers, each made of polyamide with a titer of about 44 dtex. The hairs 50 anchored when knitting the hairy yarn 40 on a crochet machine are formed by viscose yarns, each with a titer of the order of 44 dtex. The hairy yarn 40 has a titer of the order of 23,000 Nm.

Figure 6:
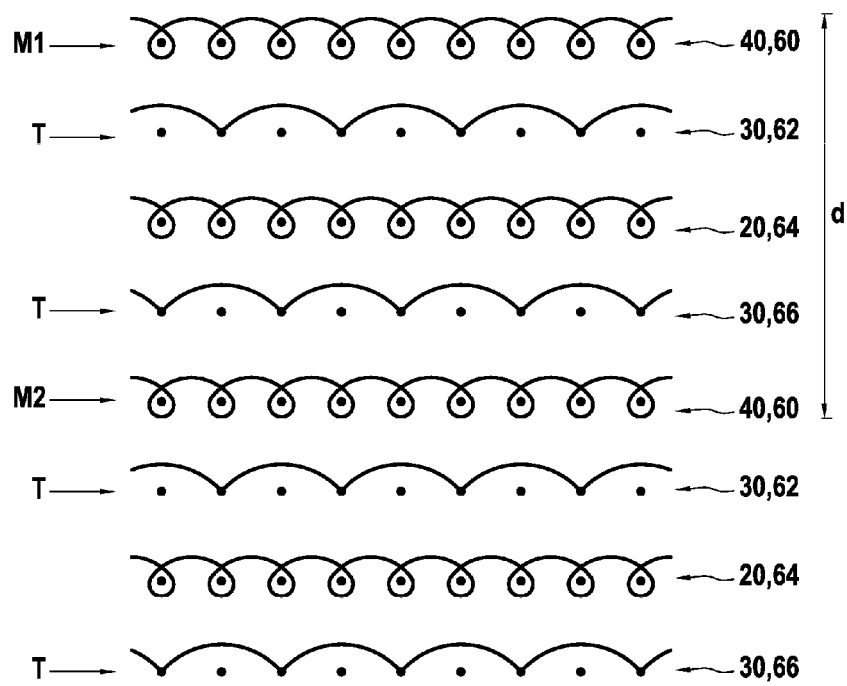
FIG. 6 is a representation of the stitch pattern shown in FIG. 3, repeated twice.

The number of sections 55 of hairs 50 per centimeter measured along the length of the hairy yarn 40 is greater than or equal to 3 and less than or equal to 10, in particular of the order of 4. The weft elastic yarn 30 comprises an elastic core of elastane with a titer of the order of 620 dtex, and two wrapped polyamide cover yarns, each of which has a titer of the order of 22 dtex. A first cover yarn is wrapped in the direction S while the second cover yarn is wrapped in the direction Z. Finally, the knitted piece 10 comprises an inlaid elastic yarn 30 arranged in a row of stitches T, as shown in FIG. 6, between two rows of stitches M1 and M2, each comprising at least one stitch hairy yarn 40, in particular the reverse side on all needles. The row of stitches T is arranged between the adjacent rows M1 and M2, and the length of at least 80% of the hairs 50 of said at least one hairy yarn 40 in one of the rows of stitches M1 and M2 is greater than or equal to the distance d between the rows of stitches M1 and M2. The distance d shown schematically in FIG. 6 is not evaluated on the knitting machine but on the relaxed knitted piece 10, in particular under the hygrometric and temperature conditions defined in the standard NF ISO 139:2005. The hairs 50 thus have, for at least 80% in number, preferably at least 95% in number, for example a length of the order of 2 mm f 7%. The hairy yarn 40 may form stitches, in particular tuck stitches and/or loop stitches, and is not inlaid. Finally, the ground yarn 20 is elastic and thus comprises an elastane core with a titer of the order of 44 dtex and two cover yarns, in particular polyamide, in particular wrapped, each with a titer of the order of 78 dtex.

Figure 3:
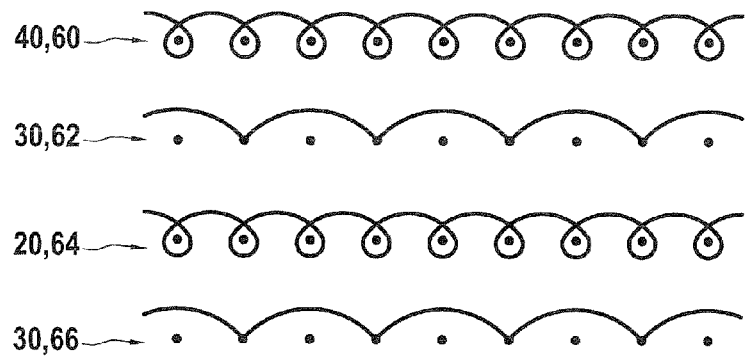
FIGS. 3 to 5 are representations of three examples of the stitch pattern of the knitted piece of the garment shown in FIG. 1.

The first example of the stitch pattern in FIG. 3 thus comprises a first row of jersey stitches 60, in particular reverse stitches, knitted on all needles with the hairy yarn 40, a second row 62 of stitches loaded every other needle knitted with the weft elastic yarn 30, a third row 64 of jersey stitches, notably reverse stitches, knitted on all the needles with the elastic stitch ground yarn 20, and finally a fourth row of tuck stitches 66 one needle out of two, staggered with the second row of tuck stitches 62, and knitted with the weft elastic yarn 30. This stitch pattern corresponds in particular to the compressive structure from the welt of the malleolus to the welt 5 of the compression garment 1, i.e., substantially to the leg part 4.

Figure 4:
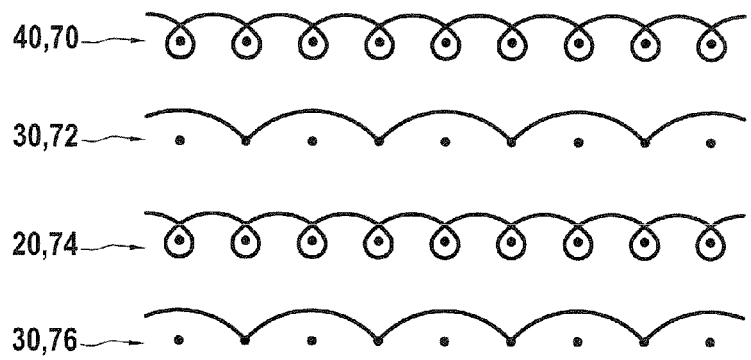

The second example of a stitch pattern in FIG. 4 includes a first row of jersey stitches 70, in particular reverse stitches, knitted on all needles with the hairy yarn 40, a second row 72 of tuck stitches every other needle knitted with the weft elastic yarn 30, a third row 74 of jersey stitches, in particular reverse stitches, knitted on all the needles with the elastic stitch ground yarn 20, and finally a fourth row of tuck stitches 76 every other needle, identical to the second row of tuck stitches 72, and knitted with the weft elastic yarn 30. This stitch pattern corresponds in particular to a ribbed structure of the compression garment 1 assigned by the weft yarn, in particular arranged at the compressive structure from the welt of the malleolus to underneath the welt 5 of the garment 1, i.e., substantially at the leg part 4.

Figure 5:
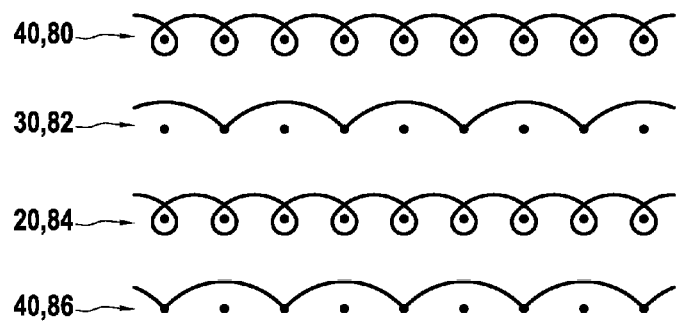

The third example of a stitch pattern in FIG. 5 includes a first row of jersey stitches 80, in particular reverse stiches, knitted on all needles with the hairy yarn 40, a second row 82 of tuck stitches every other needle knitted with the weft elastic yarn 30, a third row of 84 loop stitches every other needle, in particular reverse stitches, in the elastic stitch ground yarn 20, and finally a fourth row of tuck stitches 86 every other needle, staggered with the second row of tuck stitches 82, and knitted with the weft elastic yarn 30. This stitch pattern corresponds in particular to a ribbed structure of the compression garment 1 assigned by the elastic stitch ground yarn 20, in particular arranged at the level of the compressive structure from the welt of the malleolus to below the welt 5 of the garment 1, (i.e., corresponding substantially to the leg part 4).

Advantageously, the stitch pattern, the density and the hairs 50 length make it possible to precisely determine the desired "velvet" effect for the knitted garment 10, and thus to impact the shearing effect of the elastic yarns 30, and consequently to make the compression garment 1 easy to slip on and off. It is also possible to combine this effect with different knitted structures, for example with a ribbed effect as described above.

The invention claimed is:

1. A compression garment comprising:
a compression knitted piece comprising an inner face and an outer face, said compression knitted piece comprising at least one stitch ground yarn, and at least one elastic yarn;
wherein the compression knitted piece comprises also at least one hairy yarn comprising hairs, said at least one hairy yarn being knitted into the compression knitted piece so that the compression knitted piece comprises hairs from the at least one hairy yarn projecting from along all or part of both the inner face and the outer face of the compression knitted piece, said hairs being configured so as to be oriented in a direction in which the compression knitted piece is slipped on and/or off, and wherein the at least one hairy yarn comprises: a core comprising at least one core yarn, and at least one hairy-forming yarn anchored in the core of the at least one hairy yarn, wherein the at least one hairy-forming yarn forms sections projecting from the core of the at least one hairy yarn, wherein said sections are distributed along all or part on a length of the core of the at least one hairy yarn, wherein each of said sections comprises: a first end section joined to the core of the at least one hairy yarn, and a second free end section, wherein each of said sections forms several hairs, said hairs of all the sections forming the hairs of said at least one hairy yarn.

2. The compression garment according to claim 1, wherein the at least one core yarn is knitted in order to form a longilineal knitted core.

3. The compression garment according to claim 2, wherein the longilineal knitted core of the at least one hairy yarn is one column of pillar stitches in which the hairs are anchored.

4. The compression garment according to claim 2, wherein the at least one core yarn is chosen among: a multifilament yarn, a spun yarns of fibers, and a mixture thereof.

5. The compression garment according to claim 1, wherein a number of sections per centimeter measured along a length of the at least one hairy yarn is greater than or equal to 3.

6. The compression garment according to claim 1, wherein the compression knitted piece comprises:
a. at least one row of stitches T comprising at least one inlaid elastic yarn,
b. at least two rows of stitches M1 and M2, each comprising at least one knitting hairy yarn forming knitted stitches, said at least one row of stitches T being disposed between adjacent rows M1 and M2, and wherein a length of at least 80% by number of the hairs of said at least one hairy yarn in one of the rows of stitches M1 and M2 is greater than or equal to the distance separating the rows of stitches M1 and M2.

7. The compression garment according to claim 1, wherein a length of at least 80% by number of the hairs per centimeter, measured over a length of the at least one hairy yarn, is greater than or equal to 1 mm.

8. The compression garment according to claim 1, wherein the at least one hairy yarn is manufactured by knitting on a warp crochet knitting machine.

9. The compression garment according to claim 1, wherein the at least one hairy yarn forms at least one of tuck stitches and loop stitches.

10. The compression garment according to claim 1, wherein the compression knitted piece comprises an inlaid hairy yarn.

11. The compression garment according to claim 1, wherein the at least one elastic yarn comprises an elastic core and at least one cover yarn, and wherein the core has a titer less than or equal to 740 dtex.

12. The compression garment according to claim 1, wherein the at least one hairy yarn has a titer greater than or equal to 15,000 Nm.

13. The compression garment according to claim 1, wherein a length of at least 80% by number of the hairs per centimeter, measured over a length of the at least one hairy yarn, is greater than or equal to 5 mm.

14. The compression garment according to claim 1, wherein the number of sections per centimeter measured along a length of the at least one hairy yarn is less than or equal to 20.

15. The compression garment according to claim 1, wherein the at least one elastic yarn is inlaid.

16. The compression garment according to claim 1, wherein said second free ends are configured to adopt a direction corresponding to the direction of slipping on when the compression garment is disposed around at least a portion of a limb or slipping off when the compression garment is pulled out from the said at least portion of a limb.

17. The compression garment according to claim 1, wherein the at least one hairy yarn is inelastic.

18. A method for the manufacture of a compression garment, the compression garment being configured to facilitate slipping the compression garment on and/or off, the method comprising:
knitting a compression knitted piece with at least one hairy yarn comprising hairs, said compression knitted piece comprising an inner face and an outer face and at least one stitch ground yarn and at least one elastic yarn, said at least one hairy yarn being knitted in the compression knitted piece so that the compression knitted piece comprises hairs from the at least one hairy yarn projecting from along all or part of both the inner face and the outer face of the compression knitted piece, said hairs being arranged so as to be oriented in the direction in which the compression knitted piece is slipped on and/or off, and wherein the at least one hairy yarn comprises: a core comprising at least one core yarn, and at least one hairy-forming yarn anchored in the core of the at least one hairy yarn, wherein the at least one hairy-forming yarn forms sections projecting from the core of the at least one hairy yarn, wherein said sections are distributed along all or part on a length of the core of the at least one hairy yarn, wherein each of said sections comprises a first end section joined to the core of the at least one hairy yarn, and a second free end section, wherein each of said sections forms several hairs, said hairs of all the sections forming the hairs of said at least one hairy yarn.

19. The method according to claim 18, wherein the compression knitted piece is knitted on a circular knitting machine or on a flat knitting machine, and wherein the at least one hairy yarn is produced in a knitting step prior to the step of knitting the compression knitted piece.

20. The method according to claim 19, wherein the at least one hairy yarn is produced in a knitting step on a warp crochet knitting machine, prior to the step of knitting the compression knitted piece.

21. A compression garment comprising:
a compression knitted piece comprising an inner face and an outer face, said compression knitted piece comprising at least one stitch ground yarn, and at least one elastic yarn;
wherein the compression knitted piece comprises also at least one hairy yarn comprising hairs, said at least one hairy yarn being knitted into the compression knitted piece so that the compression knitted piece comprises hairs from the at least one hairy yarn projecting from along all or part of both the inner face and the outer face of the compression knitted piece, said hairs being configured so as to be oriented in a direction in which the compression knitted piece is slipped on and/or off, and wherein the at least one hairy yarn comprises:
a core comprising at least one core yarn, and
at least one hairy-forming yarn anchored in the core of the at least one hairy yarn,
wherein the at least one hairy-forming yarn forms sections projecting from the core of the at least one hairy yarn, wherein said sections are distributed along all or part on a length of the core of the at least one hairy yarn, wherein each of said sections comprises: a first end section joined to the core of the at least one hairy yarn, and a second free end section, and wherein each of said sections forms several hairs, said hairs of all the sections forming the hairs of said at least one hairy yarn, wherein the at least one core yarn is knitted in order to form a longilineal knitted core, wherein the longilineal knitted core of the at least one hairy yarn is one column of pillar stitches in which the hairs are anchored.

* * * * *